US012157638B2

(12) United States Patent
Siegelin et al.

(10) Patent No.: US 12,157,638 B2
(45) Date of Patent: Dec. 3, 2024

(54) SYSTEM FOR STERILIZING STERILIZATION UNITS AND METHOD FOR OPERATING SUCH A SYSTEM

(71) Applicants: FRAMATOME GmbH, Erlangen (DE); BBF STERILISATIONSSERVICE GMBH, Kernen-Rommelshausen (DE)

(72) Inventors: Steffen Siegelin, Bamberg (DE); Oswald Bieber, Heroldsbach (DE); Johannes Jandl, Remshalden (DE)

(73) Assignees: FRAMATOME GmbH, Erlangen (DE); BBF STERILISATIONSSERVICE GMBH, Kernen-Rommelshausen (DE)

( * ) Notice: Subject to any disclaimer, the term of this patent is extended or adjusted under 35 U.S.C. 154(b) by 276 days.

(21) Appl. No.: 17/609,776

(22) PCT Filed: Jun. 14, 2019

(86) PCT No.: PCT/EP2019/065720
§ 371 (c)(1),
(2) Date: Nov. 8, 2021

(87) PCT Pub. No.: WO2020/249234
PCT Pub. Date: Dec. 17, 2020

(65) Prior Publication Data
US 2022/0212878 A1 Jul. 7, 2022

(51) Int. Cl.
*B65G 25/02* (2006.01)
*A61L 2/08* (2006.01)
(52) U.S. Cl.
CPC ............. *B65G 25/02* (2013.01); *A61L 2/081* (2013.01); *A61L 2202/14* (2013.01); *B65G 2203/0216* (2013.01); *B65G 2203/0233* (2013.01)

(58) Field of Classification Search
CPC ............ B65G 25/02; B65G 2203/0216; B65G 2203/0233; A61L 2/081; A61L 2202/14; A61L 2/26; A61L 2202/24
See application file for complete search history.

(56) References Cited

U.S. PATENT DOCUMENTS 2,315,205 A * 3/1943 Herold .................. B65G 25/02
198/776
2,650,600 A * 9/1953 Davis .................. B65G 49/049
198/743
(Continued)

FOREIGN PATENT DOCUMENTS

CN 103762007 A 4/2014
CN 108726137 A 11/2018
(Continued)

OTHER PUBLICATIONS

Corresponding Search Report and Written Opinion for PCT/EP2019/065720.

Primary Examiner — Gene O Crawford
Assistant Examiner — Abby A Jorgensen
(74) Attorney, Agent, or Firm — Davidson Kappel LLC

(57) ABSTRACT

A system for sterilizing sterilization units by radiation exposure comprises a conveyance system for transporting sterilization units through a sterilizing environment along a conveying path. The conveyance system comprises at least one lifting beam conveyor with at least one stationary supporting beam and at least one movable lifting beam, which is movable with respect to the at least one stationary supporting beam in a longitudinal and a vertical direction. The at least one stationary supporting beam has a central region between two fixed bearings, which is supported via at least one tensile-loaded tensile element, which is fastened to the central region and to at least one vertical strut, which is arranged in the region of at least one of the fixed bearings, (Continued)

in such a manner that the tensile element extends in a direction diagonal to the longitudinal and the vertical direction.

24 Claims, 10 Drawing Sheets

(56) References Cited

U.S. PATENT DOCUMENTS

| | | | | |
|---|---|---|---|---|
| 3,716,222 | A * | 2/1973 | Anderson | F27B 9/207 |
| | | | | 432/235 |
| 5,958,336 | A * | 9/1999 | Duarte | A61L 2/10 |
| | | | | 250/455.11 |
| 6,177,677 | B1 * | 1/2001 | Alboresi | A61L 2/087 |
| | | | | 250/492.1 |
| 6,690,020 | B2 * | 2/2004 | Loda | A23B 4/015 |
| | | | | 250/455.11 |
| 7,247,865 | B2 * | 7/2007 | Flores | A61L 2/082 |
| | | | | 378/69 |
| 2003/0006378 | A1 | 1/2003 | Allen et al. | |
| 2008/0299002 | A1 | 12/2008 | Freeman et al. | |
| 2018/0200395 | A1 * | 7/2018 | Graves | A61L 2/24 |
| 2018/0343898 | A1 * | 12/2018 | Alzeer | A61L 2/10 |

FOREIGN PATENT DOCUMENTS

| | | | | |
|---|---|---|---|---|
| EP | 2008668 A1 | | 12/2008 | |
| GB | 2252316 A | * | 8/1992 | ........... B09B 3/0025 |
| JP | 2008237362 A | | 10/2008 | |
| WO | WO-9939750 A2 | * | 8/1999 | ............. A61L 11/00 |
| WO | WO-0185222 A1 | * | 11/2001 | ................ A61L 2/10 |
| WO | WO-2004064873 A2 | * | 8/2004 | ............ A23L 3/005 |
| WO | WO-2017192188 A1 | * | 11/2017 | ............. B65B 43/52 |

* cited by examiner

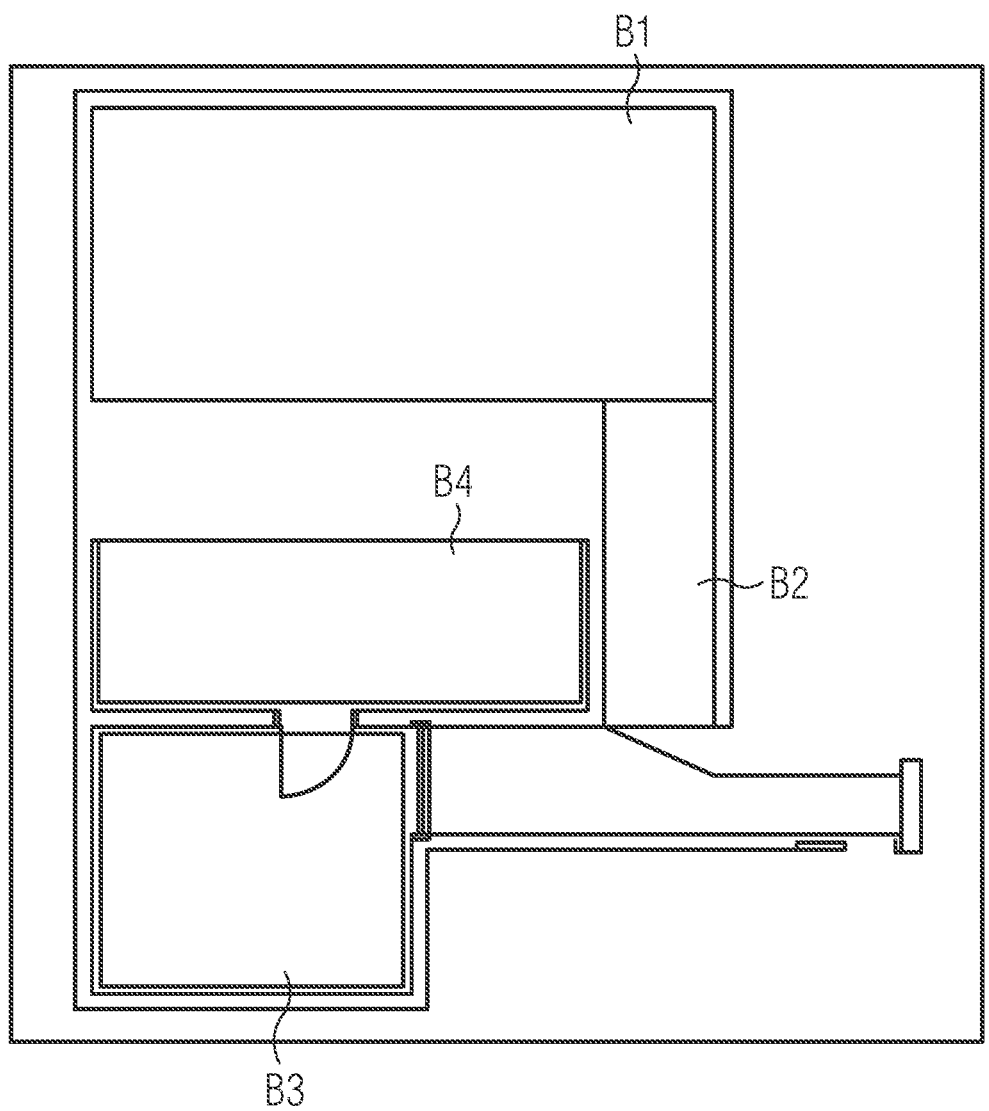

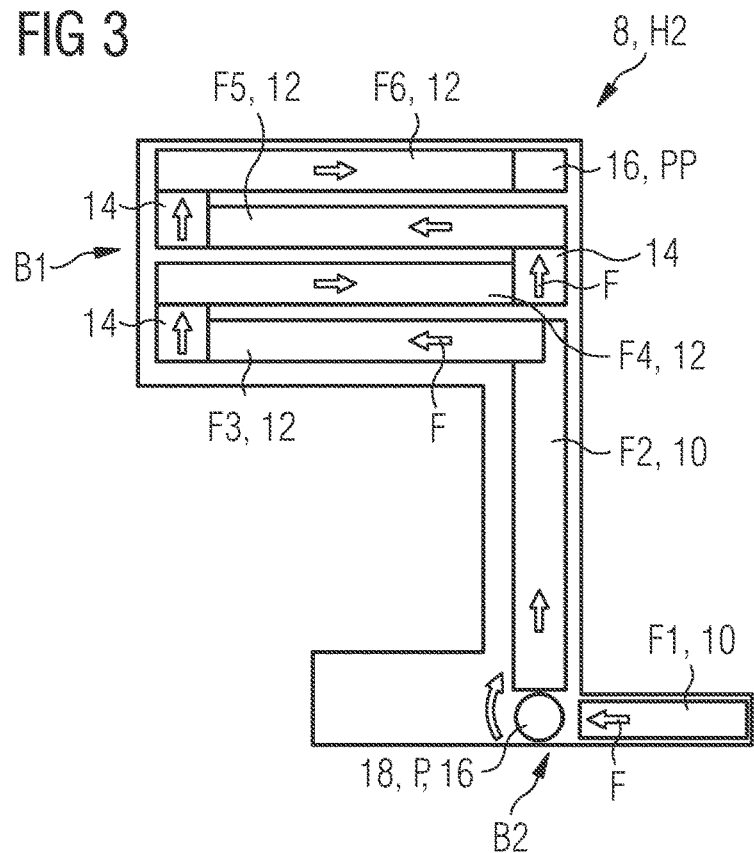
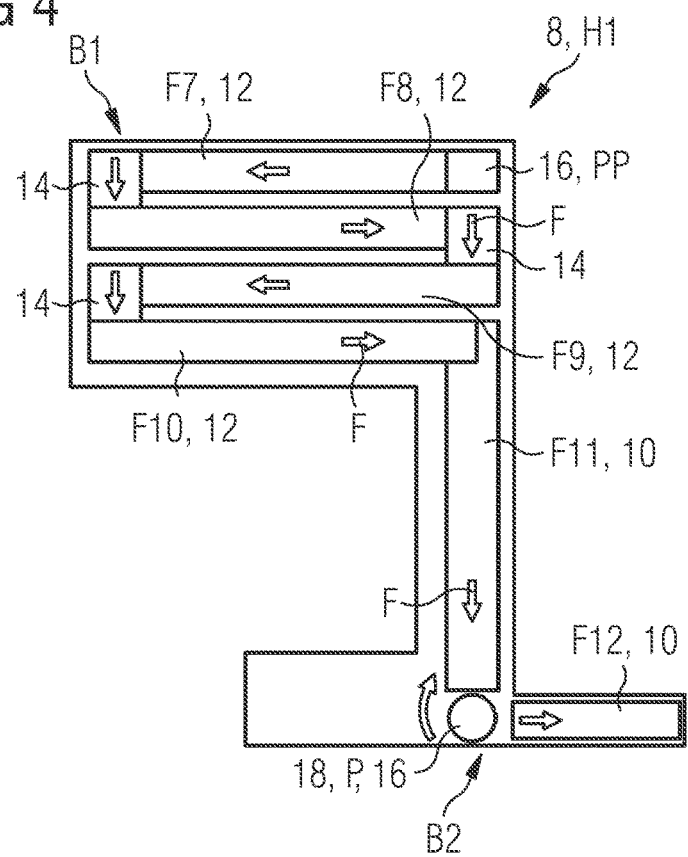

SYSTEM FOR STERILIZING STERILIZATION UNITS AND METHOD FOR OPERATING SUCH A SYSTEM

The present disclosure relates to a system for sterilizing sterilization units by radiation exposure, in particular, for sterilizing sterilization units containing medical objects by radiation exposure, which comprises a conveyance system for transporting the sterilization units through a sterilizing environment along a conveying path. The sterilizing environment is exposed to radioactive radiation from a radiation source. The conveyance system is designed in such a manner that at least one conveyance section of the conveying path extends along the periphery of the radiation source, in order to expose the sterilization units to the radioactive radiation during the transport along the conveying path. The radiation source emits gamma radiation and is realized, for example, as a Co 60 source.

The present disclosure furthermore relates to a method for operating a system, in particular, the above-mentioned system, for sterilizing sterilization units by radiation exposure, in particular, for sterilizing sterilization units containing medical objects by radiation exposure. The system comprises a conveyance system for transporting the sterilization units through a sterilizing environment along a conveying path, wherein the sterilizing environment is exposed to radioactive radiation from a radiation source emitting gamma radiation. At least one conveyance section of the conveying path extends along the periphery of the radiation source. The sterilization of the sterilization units occurs by exposure to gamma radiation from the radiation source.

BACKGROUND

It is known to expose objects for sterilization to a high-energy and, in particular, ionizing radiation, for example, UV light or radioactive radiation. In addition, systems with conveyance systems are known from the prior art, which lead the objects to be sterilized through a region or space, which is exposed to this radiation. The sterilization of the objects is thus carried out by radiation exposure.

US 2003/0006378, for example, describes a system for sterilizing objects, in which said objects are transported for the sterilization with the aid of belt conveyors into the vicinity of a radiation source emitting gamma radiation.

U.S. Pat. No. 5,958,336 describes a system for sterilizing objects, in which, for example, a lifting beam conveyor is used for transporting the objects. The sterilization takes place by irradiation with UV light.

SUMMARY

A problem addressed by the present disclosure is to indicate a system for sterilizing sterilization units, with which the sterilization can be carried out efficiently and flexibly, in particular, with respect to the application of the required target doses to the products to be sterilized.

A system for sterilizing sterilization units by radiation exposure, in particular, for sterilizing sterilization units containing medical objects by radiation exposure, comprises a conveyance system for transporting the sterilization units through a sterilizing environment along a conveying path. The sterilizing environment (also: hot cell, irradiation chamber, radiation region) is exposed to radioactive radiation from a radiation source. At least one conveyance section of the conveying path extends along the periphery of the radiation source, so that the sterilization units are exposed to radioactive radiation emitted by the radiation source during the transport along the conveying path. The radiation source emits gamma radiation and is designed, for example, as a cobalt source, in particular, as a Co 60 source.

According to the present disclosure, the conveyance system comprises at least one lifting beam conveyor with at least one stationary supporting beam and at least one movable lifting beam, which is movable with respect to the stationary supporting beam in a longitudinal and a vertical direction. The at least one stationary supporting beam has a central region between two fixed bearings, which is supported via at least one tensile-loaded tensile element. The at least one tensile element is fastened to the central region and to at least one vertical strut, which is arranged in the region at least of one of the fixed bearings in such a manner that the tensile element extends in a direction diagonal to the longitudinal and the vertical direction.

The system proposed by the present disclosure is characterized, in particular, by high efficiency and reliability, by a high speed of the conveyance system and by a high throughput of the irradiation material. In addition, a largely homogeneous irradiation of the sterilization material is ensured. The lifting beams and the supporting beams of the at least one lifting beam conveyor are preferably designed with minimal mass and positioned so that as little shielding as possible arises in the relevant irradiation region and a homogeneous dose distribution acts on the sterilization units transported along the conveying path. So that the design of the lifting beams and the supporting beams can be carried out with the minimal mass possible, the supporting beams are additionally mechanically supported by the tensile-loaded tensile elements. The diagonal arrangement of the tensile elements ensure that the shielding caused by the respective tensile element takes place at different height levels. The sterilization units are thus exposed on average to a homogeneous irradiation field, if said units are moved along the conveying path, which extends through the periphery of the radiation source.

The lifting beam conveyors used in the system are, in particular, designed in such a manner that these can be used in the immediate environment of a radiation source of high intensity with an activity of, for example, one to several million Curie (MCi range) and can be operated durably and stably in regions with, for example, a local dose rate of several kiloGray per hour (kGy/h) and ambient temperatures of up to 70° C. Bearings, drives, actuators, sensors or the like, which are used in the irradiation field, preferably consist at least in part of radiation-resistant materials and comprise, for example, fully metallic cylinders without organic seals, bearings without lubricants and sensors without electronics and organic substances.

Lifting beam conveyors can be used particularly advantageously in systems for sterilizing sterilization units, since these enable a conveyance of the irradiation material in the forward and rearward direction. In this way, the dwell time of the sterilization units in the sterilizing environment can be flexibly adapted, in order to bring about a defined radiation exposure.

In embodiments, the at least one lifting beam conveyor is operated pneumatically and comprises, in particular, at least one feed cylinder, which is designed as a drive for the longitudinal movement of the movable lifting beam, and at least one lifting cylinder, which is designed as a drive for the vertical movement of the movable lifting beam. Pneumatic drives are preferred, in particular, for the reliable operation of a high-dose environment, since these have an increased radiation resistance. Electrical drives and hydraulic drives are unsuitable for use in such a high-dose environment. Hydraulic drives typically have the disadvantage, that their hydraulic fluid, typically oil, can harden with intensive radiation exposure. The use of pneumatic drives or actuators for the drive of the lifting beam conveyer thus increases the service life and reliability of the system.

In embodiments, the tensile element is designed as a steel cable.

In embodiments, the movable lifting beam and/or stationary supporting beam is designed as a T-beam, in particular, as a double T-beam. The material proportion and the form of the supporting- and/or lifting beams are designed so that the maximum load caused by the sterilization units can be durably carried with minimal deflection. In this connection, the elastic deformation and deflection is taken into account with a sterilization unit at maximum load. In embodiments, the lifting- and supporting beams, for example, have a cantilever length, which is sufficient for bridging the basin, in which the radiation source can be lowered. The at least one lifting- and/or supporting beam, therefore, has a carrier profile, which is designed so that as little material as possible is located between the radiation source and the sterilization material. In the possible embodiments, the lifting- and supporting beams in each case have double T profiles with a cantilever length between the bearings of more than 4 m. The dimensions of the lifting- and supporting beams are designed in possible embodiments so that a maximum load of 1000 kg can be carried and the elastic deformation of the respective lifting- or supporting beam is relatively low at maximum load, in particular, less than 20 mm. The low material usage has the consequence that a low shielding effect operates between the radiation source and the sterilization units. The radiation field provided by the radiation source is thus optimally utilized and the radiation of the sterilization units takes place substantially homogenously.

In embodiments, the central region is supported by at least two tensile elements, which are fastened to opposite vertical struts, which are arranged respectively in the region of one of the fixed bearings. The support of the central region occurs, in particular, from at least two sides, wherein the tensile elements in each case extend diagonally to the conveying direction, in order to prevent undesired shielding effects as much as possible.

In embodiments, the radiation source is stored in a basin filled with water when the system is inactive. The lifting device is designed to lift the radiation source out of the basin filled with water and to lower it into the basin filled with water.

In embodiments, the conveying path has at least two conveyance sections, which extend in horizontal planes, which are spaced apart from one another in the vertical direction. These embodiments serve for the better utilization of the radiation field provided by the radiation source. In addition, a transport of the sterilization units in several horizontal planes is advantageous, since thus the possibility of multiple circulations around the radiation source is created for individually selected sterilization units, that is, individually selected sterilization units can be guided several times around the radiation source as required on a horizontal plane provided for this purpose, in order to deposit a higher dose energy, wherein the continuous operation of the system does not have to be interrupted. In particular, it is possible to apply different dose energies in the continuous operation of the system. By means of the arrangement of the conveying path in several (any desired number of) horizontal planes the partial loading of the conveyance system is made possible and no complete emptying of the system is necessary for the irradiation of sterilization units with different doses.

In embodiments, the conveying path has at least two conveyance sections arranged above one another in the vertical direction and aligned parallel to one another. The conveyance sections arranged above one another extend within the sterilization environment along the periphery of the radiation source, in order to optimally use the space available within the sterilizing environment.

In embodiments, the at least two conveyance sections arranged above one another are connected via at least one lift, which is designed to transport sterilization units to be conveyed in the vertical direction. Vertical lifts are advantageous with regard to the better utilization of the space, in particular, with respect to the radiation field provided by the radiation source. In addition, the lifts serve for the realization of several circulations, if necessary, of the sterilization units or of the irradiation material within the hot cell, in particular, depending on the desired target dose. In embodiments, it is provided, in particular, to convey sterilization units individually selected and identified by sensor with the aid of the lift back to the beginning of a path segment of the conveying path, which extends through the sterilizing environment of the radiation source.

In embodiments, the at least one lift is designed as a pneumatic lift. As already mentioned, pneumatic drives or actuators ae preferred, in particular, for the reliable operation in a high-dose environment, since these, in particular, in comparison to electrical or hydraulic drives or actuators have an increased radiation resistance.

In embodiments, the at least two conveyance sections arranged above one another in the vertical direction and aligned parallel to one another are realized or designed as lifting beam conveyers with in each case stationary supporting beams and movable lifting beams. A lifting movement of the movable lifting beams arranged above one another in the vertical direction is driven with the aid at least of one common lifting cylinder. In this way, a compact design is proposed, in which the lifting movement, in particular, of all lifting beams arranged above one another is operated with the aid of the same lifting cylinder.

In embodiments, the conveying path has at least two conveyance sections arranged in a horizontal plane and extending parallel to one another, wherein, in particular, the radiation source is arranged between the at least two conveyance sections extending parallel to one another. Preferably, the conveying path is designed in such a manner that conveyance sections provided for transporting sterilization units to be irradiated extend on both sides of the radiation source or the radiation source is circumferentially surrounded at least in part by conveyance sections of the conveying path. In this way, the field irradiated by the radiation source is better utilized.

In embodiments, the conveying path has at least one conveyance section, which comprises a roller conveyor.

In embodiments, the conveying path has at least one conveyance section, which comprises a rotary plate.

In embodiments, the rotary plate is designed as a lift or is arranged on the lift.

In embodiments, a pneumatically driven transverse slide is designed to convey the sterilization units by translational movement over a section of the conveying path. As already mentioned, pneumatic drives or actuators are preferred, in particular, for the reliable operation in a high-dose environment, since these have an increased radiation resistance, in particular, compared to electrical or hydraulic drives or actuators. It has been shown, that a rotation of the sterilization units, in particular, within the sterilizing environment is undesired, since the sterilization units are irradiated uniformly from all sides, if the sterilization units are moved in the same orientation around the radiation source. This favors the use of the transverse slide, which is designed to convey the sterilization units by translational movement. The orientation of the sterilization units in the space is not changed during the translational movement. The transverse slides are in addition a space-saving solution, in order to transport the sterilization units, in particular, from one lifting beam conveyor to the next lifting beam conveyor.

In embodiments, at least one registration device is arranged at the entrance of the conveying path, which is designed, to read out coded information, which is assigned to the sterilization units to be sterilized. The registration device registers, for example, the sterilization units arriving in a goods receiving area of the system.

In embodiments, the registration device is designed to read out optically coded information, which is applied to the sterilization units. The coded information is optically coded, for example, as a barcode or QR code. In other embodiments, RFID tags, transponders or other electronically or electromagnetically readable means are designed as carriers of the coded information. Accordingly, the registration device in such embodiments is designed as a reading device for reading out electromagnetic fields.

In embodiments, sensors are arranged along the conveying path, in particular, within the sterilizing environment, which are designed to detect data, in particular, position data, which contain information about the progress of the transport of the respective sterilization unit.

In embodiments, the registration device and/or the sensors are connected to a control device. The control device is designed to adapt at least one process parameter, in particular, conveying speed (clock cycle), irradiation time, and/or number of the circulations in the sterilizing environment, of the system, depending on the read-out coded information and/or the data detected by sensor, in particular, depending on the position data and/or depending on the dose energy to be applied. The control device calculates, in particular, the dwell time of the sterilization unit within the sterilizing region depending on the assigned target dose.

The present disclosure furthermore provides to a method for operating a system, in particular, a method for operating the system already described above, for sterilizing sterilization units by radiation exposure, in particular, for sterilizing sterilization units containing medical objects by radiation exposure. The system comprises a conveyance system for transporting the sterilization units through a sterilizing environment along a conveying path. The sterilizing environment is exposed to radioactive radiation from a radiation source. At least one conveyance section of the conveying path extends along the periphery of the radiation source.

According to the present disclosure, the sterilization of the sterilization units occurs by exposure to gamma radiation. The sterilization units are transported at least in sections along the conveying path by means at least of one lifting beam conveyor, which comprises at least one stationary supporting beam and at least one movable lifting beam, which is movable with respect to the stationary supporting beam in a longitudinal and a vertical direction. The sterilization units are individually exposed to different dose energies in the continuous operation of the system, wherein the continuous radiation cycle is not interrupted.

The proposed method realizes the sterilizing of the sterilization units with the aid of a radiation source, in such a manner that individual target doses can be applied to individual sterilization units with one and the same conveyance system, without thereby interrupting the irradiation cycle. Thus, a continuous operation of the system is ensured. The system, in particular, does not have to be emptied, in order to apply different target doses, since the lifting beam conveyors can be individually controlled, in particular, with regards to their clock frequency and conveying speed, in particular, by the control device. A control of the lifting beam conveyor for conveying the sterilization units over at least one section of the conveying path can take place, in particular, such that the transport occurs in or counter to a conveying direction.

In embodiments, coded information, in particular, optically coded information, is assigned individually to each sterilization unit. The coded information is read out at least at the entrance of the conveyance system and characterizes at least one dose energy or target dose to be applied. The coded information can exist in an optically coded manner, in particular, in the form of barcodes or QR codes. In embodiments, the sterilization units coded in this way are read-in at the goods receiving area, for example, with the aid of a registration device, in particular, with the aid of a barcode or a QR code scanner. The coded information defines which target dose or dose energy to be applied is assigned to the individual sterilization units. In addition, the coded information can clearly define the identity of the respective sterilization unit, so that, in particular, the path of the sterilization units in the irradiation region can be individually monitored and traced.

In embodiments, a control device determines a process parameter, in particular, conveying speed, irradiation time, length of the conveying path in the sterilizing environment and/or number of the circulations in the sterilizing environment, of the system, depending on the detected or read-out coded information. The control or control device determines in embodiments, for example, how many circulations the sterilization unit has to spend in the irradiation chamber, in order to reach a predetermined target dose. In a possible embodiment, the dose energy per circulation corresponds to several kiloGray, for example, approximately 6.25 kGy. In embodiments, the dose energy applied per circulation is determined in advance by means of a reference run. For this purpose, a reference run can take place, in particular, with a sterilization unit, which has an integrated dosimeter. The data detected in the reference run serve as the basis of the control and are, for example, stored in a storage medium of the control device. The control device determines, in particular, the necessary clock cycle, therefore, the irradiation time of the respective sterilization unit at an irradiation position. For example, it is determined how many of the circulations around the radiation source are required, in order to apply the predetermined target dose. The control or control device thereby calculates, in particular, the burn-up of the radiation source, which preferably is taken into account, in particular, continuously, for the current irradiation cycle. Preferably, a fail-safe control monitors the clock cycle in the individual irradiation positions and the number of circulations around the radiation source for each sterilization unit. The irradiation time (effective length of stay in the radiation field) is preferably continuously monitored by the fail-safe control. In the event a problem is detected, the conveyance system is preferably automatically stopped, the radiation source is automatically lowered into the basin and an error message is output optically or acoustically via suitable output means.

In embodiments, the position of the sterilization units along the conveying path, in particular, within the sterilizing environment, is detected by sensor. The sensory detection of the individual sterilization units takes place, in particular, in order to monitor the conveyance system as part of the fail-safe control described above. Alternatively, or additionally, the sensory detection of the sterilization units takes place, in order to adapt a process parameter. Thus, for example, a sterilization unit, to which a higher target dose is assigned, can be detected with regards to its position and depending on the already applied dose energy be automatically transported further for undergoing additional circulations around the radiation source or in the direction of a goods issuing area of the conveyance system.

BRIEF SUMMARY OF THE DRAWINGS

The present disclosure is also elucidated in detail below with regard to further features and advantages by means of the description of embodiments and with reference to the attached drawing.

FIG. 2 shows the outline of a possible room layout for a system according to an embodiment;

FIG. 3 shows the course of a conveying path of the system for sterilizing sterilization units according to an embodiment in an upper horizontal plane in a schematic top view;

FIG. 4 shows the course of a conveying path of the system for sterilizing sterilization units according to an embodiment in a lower horizontal plane in a schematic top view;

DETAILED DESCRIPTION

Parts which are the same or correspond to each other are provided in all of the figures with the same reference signs.

Figure 1:
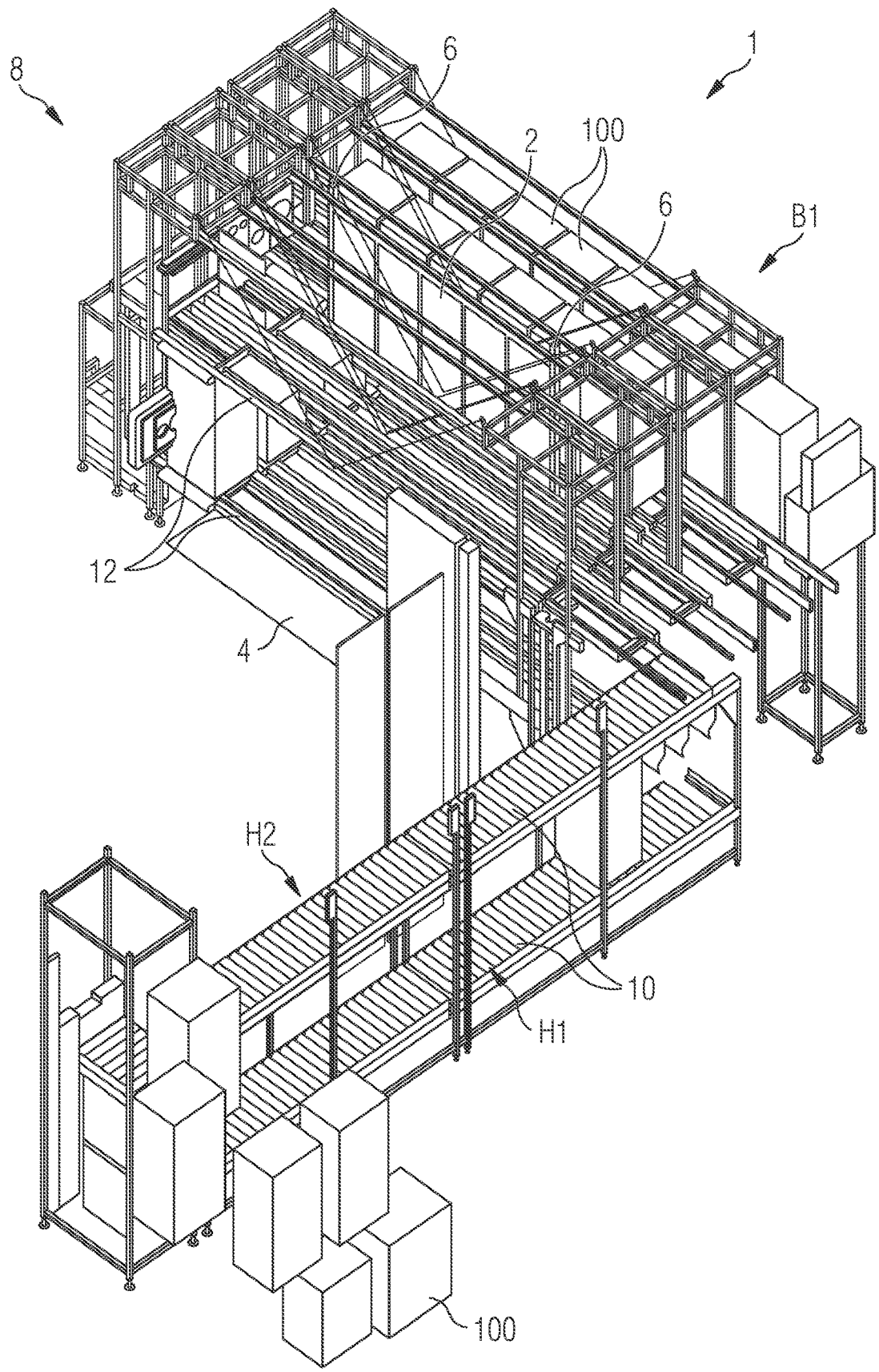
FIG. 1 shows a system for sterilizing sterilization units according to a possible embodiment in a perspective representation.

FIG. 1 shows exemplarily a system 1 for sterilizing sterilization units 100 (also: irradiation bundles) by radiation exposure. The system 1 is housed in a building. The irradiation of the sterilization units 100 takes place in a shielded room, which is referred to as "hot cell" B1. In the hot cell B1, a radiation source 2 is located, for example, a cobalt source (Co 60 source), which emits gamma radiation. The radiation source 2 is wet-stored, that is, when the system 1 is inactive, the radiation source 2 is lowered into a basin 4 containing water. A pneumatically operated lifting device 6 is provided for lowering the radiation source 2 into the basin 4 or for lifting the radiation source 2 out of the basin 4.

The sterilization of sterilization units 100 takes place by irradiation with gamma radiation from the radiation source 2. For this purpose, a conveyance system 8 is provided, in particular, in the room B1, which conveys the sterilization units 100 along a conveying path, which lies within the periphery of the radiation source 2.

The system 1 comprises, in particular, the hot cell B1, the conveyance system 8, the radiation source 2 and typically additionally, as shown, in particular, schematically in FIG. 2, a machine room B4, a control room B3 or a control of the system 1 and measuring systems.

The radiation source 2 of the embodiment shown comprises several cobalt rods, which are placed during operation in a grid between two shields in the middle of the conveyance system 8. Outside of the sterilization operation the radiation source 2 is located in the basin 4 underneath the conveyance system 8, into which the radiation source 2 can be lowered or from which it can be lifted with the aid of the lifting device 6. The basin region underneath the radiation source 2 is always open. The remaining part of the basin 4 is covered, in order to ensure a best-possible personnel protection when the radiation source 2 is lowered.

The conveyance system 8 comprises roller conveyors 10 and lifting beam conveyors 12 (also: "walking beam"), which in each case form conveyance sections of a conveying path, along which the sterilization units 100 are transported during the operation of the system 1. As shown, in particular, in FIG. 1, the conveying path runs within the hot cell B1 in a meandering manner around the radiation source 2. The conveying path is arranged in the example shown exemplarily in two horizontal planes H1, H2, which are spaced apart from one another in the vertical direction. In other embodiments, the conveying path can run, in particular, on more than two planes spaced apart from one another in the vertical direction. In order to convey sterilization units 100 between the different horizontal planes H1, H2, lifts 16 are provided, which are designed to convey the sterilization units 100 accordingly in the vertical direction.

Within the hot cell B1 the conveyance of the sterilization units 100 takes place by means of lifting beam conveyors 12. Outside of the hot cell B1, in particular, in the region B2 (see, in particular, FIG. 2), which corresponds to an irradiation chamber with low local dose rate, roller conveyors 10 are arranged for conveying the objects sterilized or to be sterilized.

FIGS. 3 and 4 show the course of the conveying path in a schematic top view. FIG. 3 thereby shows the course of the conveying path in the upper horizontal plane H2. Accordingly, FIG. 4 shows the course of the conveying path in the lower horizontal plane H1.

The upper horizontal plane H2 is designed, for example, for the transport of the sterilization units 100 into the hot cell B1. Accordingly, the lower horizontal plane H1 is designed for the transport of the sterilization units 100 out of the hot cell B1. However, the conveyance system 8 can thereby be designed, in particular, to realize the transport in the correspondingly opposite conveyance direction. The conveyance direction F is illustrated in FIG. 3 and FIG. 4 schematically by means of arrows.

The conveying path of the conveyance system 8 in the upper horizontal plane H2 comprises conveyance sections F1 to F6. The conveying path of the conveyance system 8 in the lower horizontal plane H1 comprises conveyance sections F7 to F12. The conveyance sections F1 and F12 or F2 and F11 or F3 and F10 or F4 and F9 or F5 and F8 or F6 and F7 in each case lie above one another and extend parallel to one another. The conveyance sections F1, F2, F11 and F12 extend through the region B2 (see, in particular, FIG. 2) and are designed as roller conveyors 10. The conveyance sections F3 to F10 extend in a meandering manner through the hot cell B1 (see, in particular, FIGS. 1 and 2) and are designed as lifting beam conveyors 12. In each case a transverse slide 14 is arranged on the end side of the conveyance section F3, F4, F5, F7, F8, F9, which transverse slide is designed to convey the sterilization units 100 by translational movement to a conveyance section F4, F5, F6, F8, F9, F10 following in the conveyance direction F, without thereby changing the orientation of the sterilization units 100 within the hot cell B1. This is advantageous, since, a uniform irradiation of the sterilization units 100 is thus ensured on all sides.

In the design illustrated exemplarily in FIGS. 3 and 4, a transverse slide 14 is provided, which is designed to convey sterilization units 100 from the conveyance section F3 to the conveyance section F4. Further transvers slides 14 are designed to convey sterilization units 100 from the conveyance section F4 to the conveyance section F5 or from the conveyance section F5 to the conveyance section F6 or from the conveyance section F7 to the conveyance section F8 or from the conveyance section F8 to the conveyance section F9 or from the conveyance section F9 to the conveyance section F10.

The lower and the upper horizontal planes H1, H2 are connected by lifts 16, which make possible the conveyance of the sterilization units in the vertical direction. Rotary plates 18 are arranged on the lift 16 at the input-side position P, which makes possible a rotation of the sterilization units 100 in the region B2, therefore, outside of the irradiation field of the hot cell B1. The lift 16 at the position P also makes possible a multiple circulation around the radiation source 2, in particular, corresponding to a target dose or dose energy individually assigned to the sterilization unit 100 to be sterilized.

Within the hot cell B1 the conveying path is formed by lifting beam conveyor 12, so that the sterilization units 100 can be conveyed, if necessary, also counter to the conveyance direction F, in particular, in order to ensure an irradiation corresponding to a predetermined dose energy or target dose.

The lift 16 arranged on the end side at the position PP connects the conveyance sections F1 to F6 of the lower horizontal plane H1 to the conveyance sections F7 to F12 of the upper horizontal plane H2.

Figure 5:
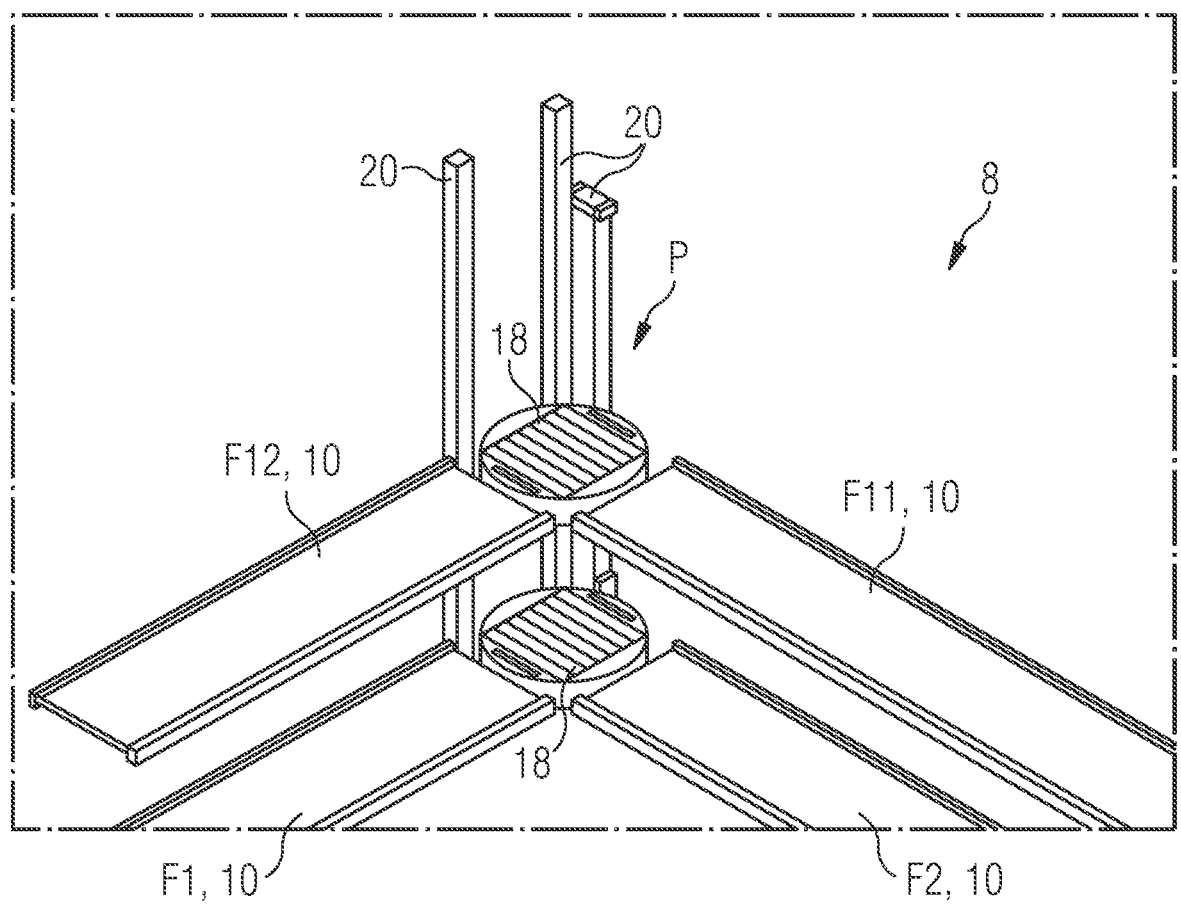
FIG. 5 shows a section of a conveyance system for the system for sterilizing sterilization units with a lift and rotary plate according to an embodiment in a perspective representation.

In the lift 16 at position P, two rotary plates 18 are provided for realizing the multiple circulation, which rotary plates are shown in detail in the perspective representation of FIG. 5. The rotary plates 18 are guided movably in the vertical direction along the rails 20. The rotary plates 18 are in each case provided with a rotary drive and a feed drive 22, which, in particular, serve two purposes during the conveying operation in the system 1. On the one hand, the rotary plates 18 are designed to move sterilization units 100 from the conveyance section F1 or F11 formed by the roller conveyor 10 to the conveyance section F2 or F12, which is also formed by a roller conveyor 10. A motor-assisted 90° rotation of the respective rotary plate 19 thereby takes place.

The feed drive 22, which is also designed in the manner of a motor-assisted roller conveyor, serves for transporting the sterilization units 100 from the respective rotary plate 18 to the respective roller conveyor 10.

Furthermore, the rotary plates 18 serve to convey sterilization units 100, which were not yet irradiated in a pass through the hot cell B1 with the predetermined dose energy or target dose, back to the beginning of the conveying path through the hot cell B1. This occurs in the embodiment shown in that the corresponding sterilization units 100 are conveyed by means of the lift 18 at the position P of the lower horizontal plane H1 back to the upper horizontal plane H2. The rotary plate 18 thereby conveys the corresponding sterilization unit 100 through a lifting movement in the vertical direction upwards. During this process, the addition of further sterilization units 100 is preferably stopped, in order to prevent an inadmissible loading of the roller conveyor 10.

Figure 6:
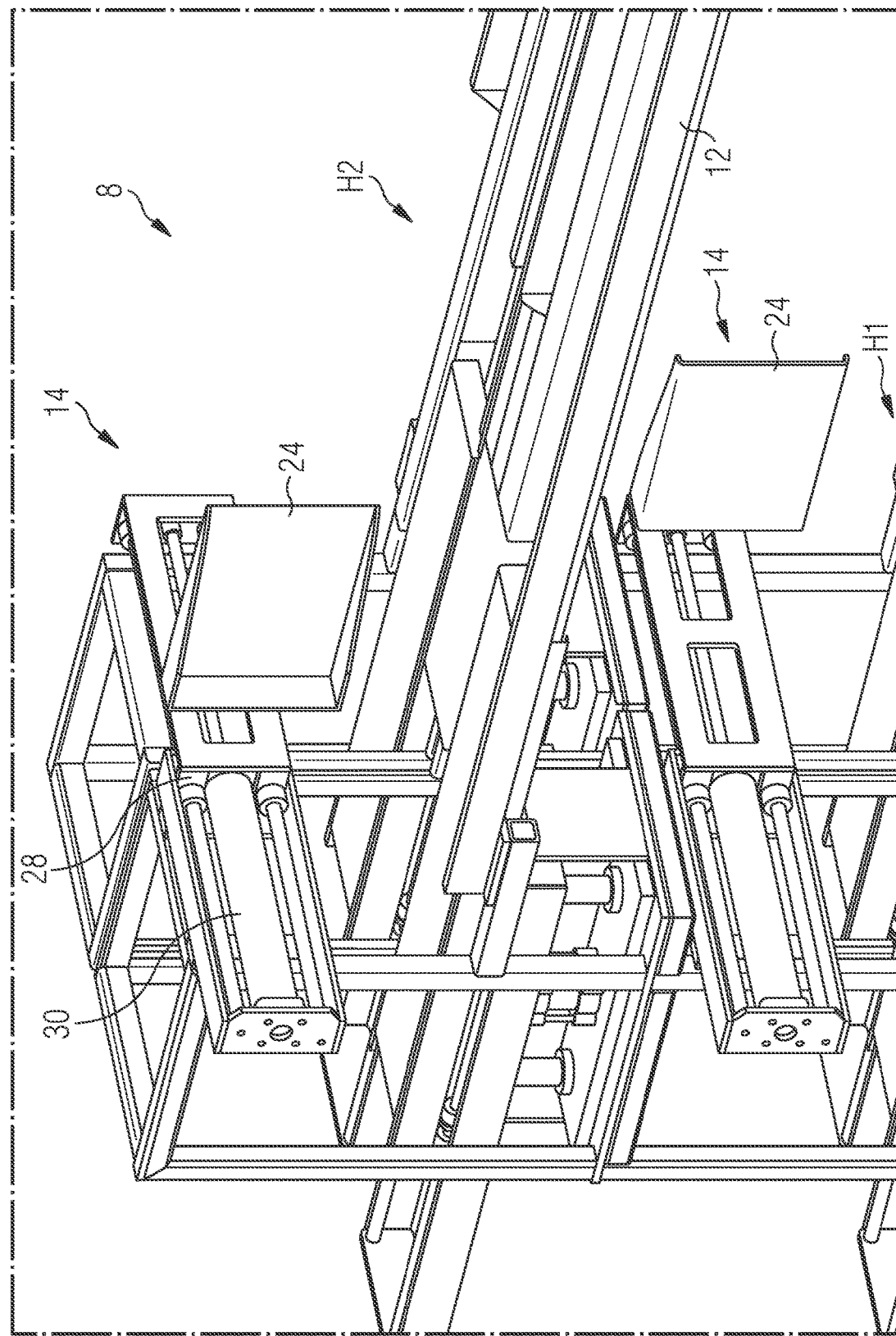
FIG. 6 shows a section of a conveyance system for the system for sterilizing sterilization units with a transverse slide according to an embodiment in a perspective representation.

FIG. 6 shows details of the transverse slide 14 in a perspective representation. In order to exert a force on the sterilization units 100 to be transported, the transverse slides 14 have stamps 24, which are guided in a guide 28 in a linearly movable manner and are pneumatically driven by push cylinder 30.

During operation, the pneumatically operated stamps 24 push the sterilization units 100 with their flat side onto the next conveyance section F4, F5, F6, F8, F9, F10 in the conveyance direction F, which is designed as lifting beam conveyor 12. One sterilization unit 100 is thereby moved per clocking step and the stamp 24 is brought back into the starting position. The stamps 24 in the lower horizontal plane H1 are arranged with respect to stamps 24 in the upper horizontal plane H2 in the opposite direction.

FIGS. 7A to 7D illustrate the operating mode of the lifting beam conveyor 12 in perspective representations.

The lifting beam conveyor 12 according to the embodiment depicted comprises two stationary supporting beams 32 arranged parallel to one another and two lifting beams 34 arranged parallel to one another. The lifting beams 34 are driven pneumatically and are guided movably relative to the supporting beam 32 both in the vertical direction as well as in the longitudinal direction, therefore in a direction along the longitudinal extent of the supporting beam. Pneumatic feed cylinders 36 are provided as drive for the movement of the lifting beams 34 in the longitudinal direction. Accordingly, pneumatic lifting cylinders 38 are provided as drive for the movement of the lifting beams 34 in the vertical direction. In embodiments, in which several lifting beam conveyors 12 are arranged in the vertical direction lying above one another, it is provided in an advantageous manner, to couple the lifting beams 34 lying above one another to each other. In this way, it is made possible to drive the lifting movement of the lifting beams 34 lying above one another with the same lifting cylinders 38. It is thus not absolutely necessary to provide separate lifting cylinder 38 for each of the lifting beam conveyors 38 lying above one another. This applies in particular to any desired number of conveyor tracks arranged above one another with lifting beam conveyors 12.

The function of the lifting beam conveyor 12 is to transport the sterilization units 100, in particular, from the roller conveyers 10 and the transverse slides 14 on and over the supporting beams 32. This is done in four steps, which are illustrated accordingly in FIGS. 7A to 7D.

Figure 7A:
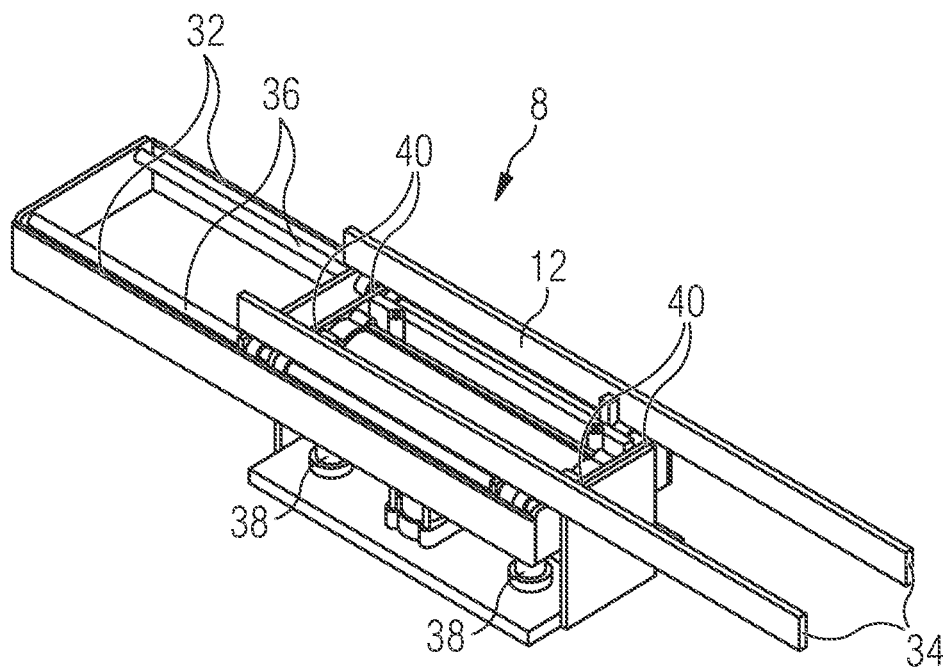
FIG. 7A shows a perspective representation of a lifting beam conveyor for the conveyance system according to a possible embodiment in a first position.
Figure 7B:
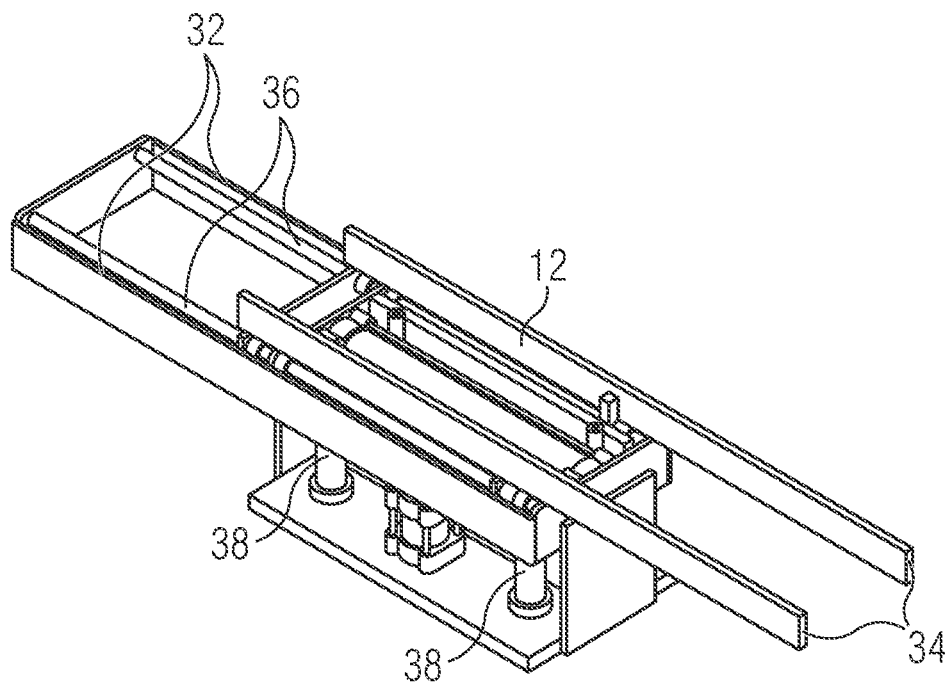
FIG. 7B shows a perspective representation of a lifting beam conveyor for the conveyance system according to a possible embodiment in a second position.

The starting position is the position depicted in FIG. 7A. In a first step a movement of the lifting beams 34 takes place in the vertical direction, wherein the movable lifting beams 34 are moved upwards relative to the upper support edge of the supporting bar 32 by a few centimeters, for example, by about 3 cm. The sterilization units 100 resting on the supporting beam 32 are thereby lifted. The resulting positioning, in particular, of the lifting beams 34 relative to the supporting beams 32 is depicted in FIG. 7B.

Figure 7C:
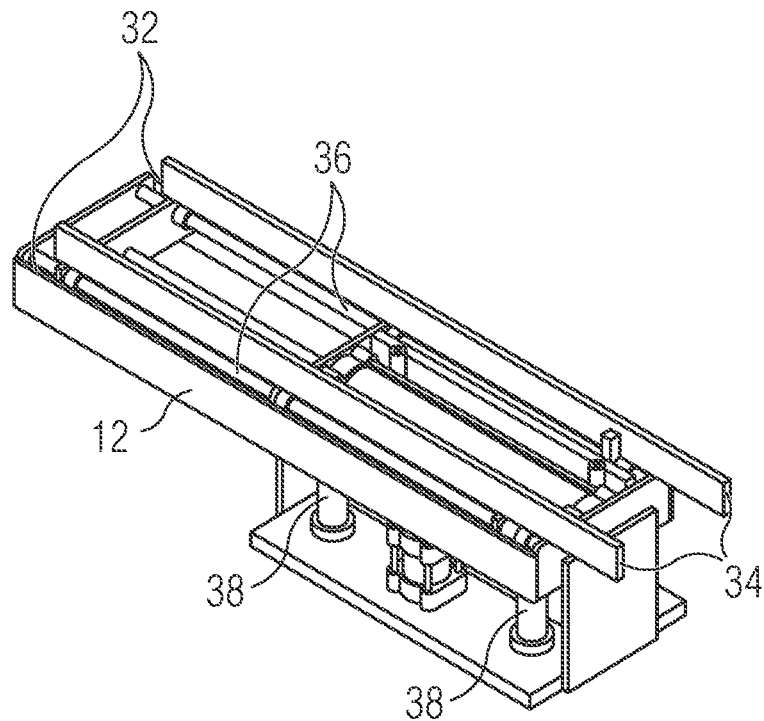
FIG. 7C shows a perspective representation of a lifting beam conveyor for the conveyance system according to a possible embodiment in a third position.

In a second step, the conveying stroke occurs in the direction of the conveyance direction F. Here, the feed cylinders 36 extend corresponding to the conveyor length per clock step preferably by several 10 cm, for example, by approximately 60 cm horizontally in the longitudinal direction, in order to move the lifting beam 34 accordingly by said conveyor length in the conveyance direction F. The resulting positioning, in particular, of the lifting beams 34 relative to the supporting beams 32 is depicted in FIG. 7C.

Figure 7D:
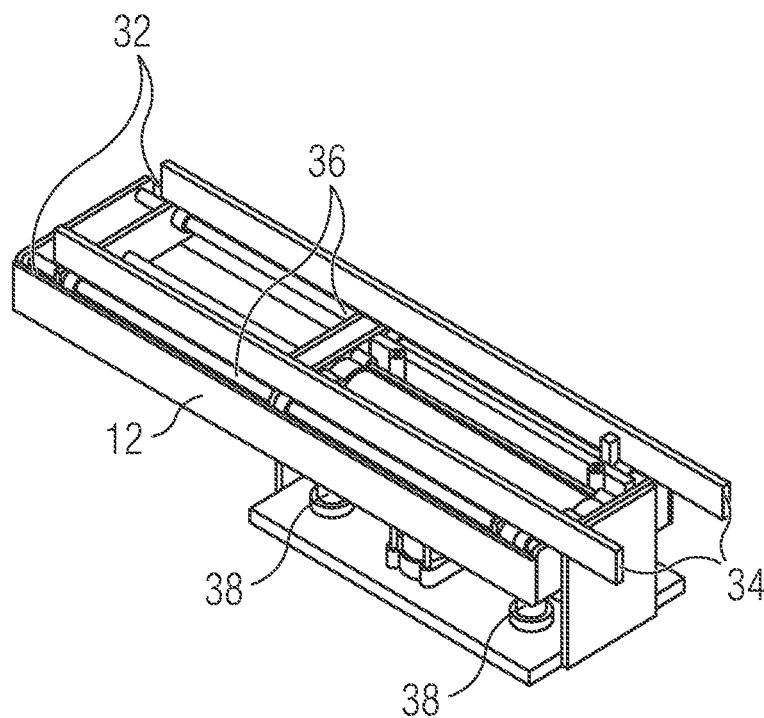
FIG. 7D shows a perspective representation of a lifting beam conveyor for the conveyance system according to a possible embodiment in a fourth position.

In a third step, sterilization units 100 are stored again by lowering the lifting cylinder 38 and accordingly the lifting beams 34 onto the stationary supporting beams 32. The movable lifting beams 34 are, in this connection, lowered under the stationary supporting beams 32, for example, in such a manner that the upper support edge of the lifting beams 34 are located a few millimeters, in particular, about 5 mm, underneath the upper support edge of the supporting bar 32. The resulting positioning, in particular, of the lifting beams 34 relative to the supporting beams 32 is depicted in FIG. 7D.

In a fourth step, the lifting beams 34 are moved back through the feed cylinder 36 into the starting position (FIG. 7A).

The retraction and/or extension speed of the feed cylinder 36 and/or the lifting cylinder 38—and thus the conveyance speed along the lifting beam conveyor 12—can be set by regulation of the compressed air.

The lifting beams 34 are stored on supports 40 and by means of counter-supports arranged outside of the relevant radiation field of the radiation source 2. The lifting beams 34 and the supporting beams 32 are designed as T-beams or double T-beams. In order to further increase the mechanical stability, the supporting beams 32 are supported in a central region by tensile-loaded tensile elements 42. This is depicted in the section enlargement of FIG. 8.

Figure 8:
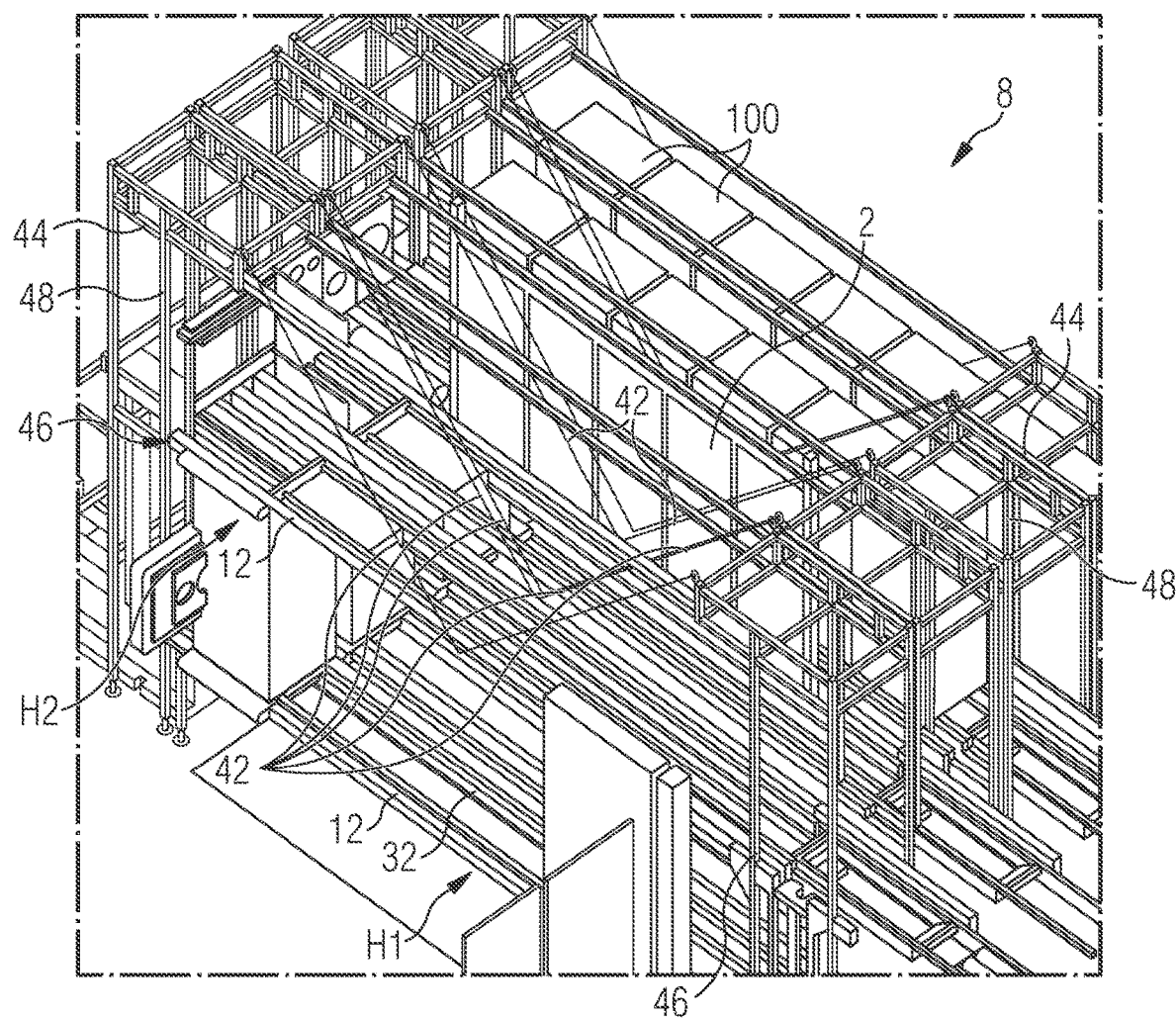
FIG. 8 shows an enlarged section of FIG. 1.

FIG. 8 shows an enlarged section of FIG. 1. The supporting beams 32 are in each case fastened fixedly to a frame 44 on the end side, which frame thus forms a fixed bearing 46 for the respective supporting beams 32. The frame 44 furthermore comprises vertical struts 48, to which the tensile elements 42, which are realized in the embodiment by steel cables, are fastened. The tensile elements 42 are tensioned between the central regions of the respective supporting beams 34, which are located approximately centrally between the fixed bearings 46 formed by the frame 44, and the upper end of the frame 44. The tensile element 42 thus extends in a direction diagonal to the longitudinal and the vertical direction. Thus, it is achieved that the tensile elements 42 are not located at the same height level, in order to avoid disadvantageous shielding effects during the sterilization of the sterilization units 100, if these are conveyed along the conveying path around the radiation source 2.

Coded information is assigned to the individual sterilization units 100, which specifies the individual sterilization process. In addition, the coded information contains, in particular, individual identification information, so that the conveyance process of the respective sterilization unit 100 can be monitored. The coding takes place, for example, optically, in particular, with the aid of a label, which is provided with a barcode or a QR code and is applied to the sterilization unit 100. The coded information contains, in particular, an item of identification information, for example, in the form of a registration number and/or a job-ID, an irradiation prescription, which, for example, defines a target dose to be applied, dose energy, dose per circulation and/or packaging density, information about the necessary number of circulations around the radiation source 2 and/or information about the type of container of the respective sterilization unit 100.

The coded information or the irradiation prescription, in particular, defines process parameters for the subsequent irradiation of the sterilization units 100. The number of circulations around the radiation source 2 and/or the clock cycle can be determined depending on a source activity prevailing at the time of the irradiation, taking into consideration a target dose to be applied (required target dose in the dose minimum) and the maximum density of the irradiation material (sterilization unit 100).

In a possible embodiment of the system 1, the maximum density of the irradiation material is approximately 0.25 $g/cm^3$ and the smallest possible target dose, which must be achieved in the event of an exemplary source activity of 2 MCi and a density of the irradiation material of 0.25 $g/cm^3$ in the dose minimum in the event of a single circulation around the radiation source 2, is approximately ≤6.25 kGy. In a possible embodiment of the system 1, the result is, for example, a maximum circulation number of four source circulations at a target dose of ≤25 kGy in the dose minimum.

When defining the process parameters, the clock cycle is optionally predetermined by the user or automatically calculated for the respective application time by a control. As part of an irradiation process, therefore, as part of a passage of a sterilization unit 100 through the hot cell B1, the number of circulations of the sterilization unit 100 around the radiation source 2 is individually determined, for example, depending on an assigned target dose. Based on the density of the irradiation unit of 0.25 $g/cm^3$, a source activity of 2 MCi and a fourfold circulation of the sterilization unit 100 around the radiation source 2, the conveyance system 8 of a possible embodiment is designed, for example, for a conveyance speed, which ensures the application of a target dose of ≤25 kGy in the dose minimum after completion of the irradiation process, that is, when leaving the hot cell at the cell exit.

Figure 9:
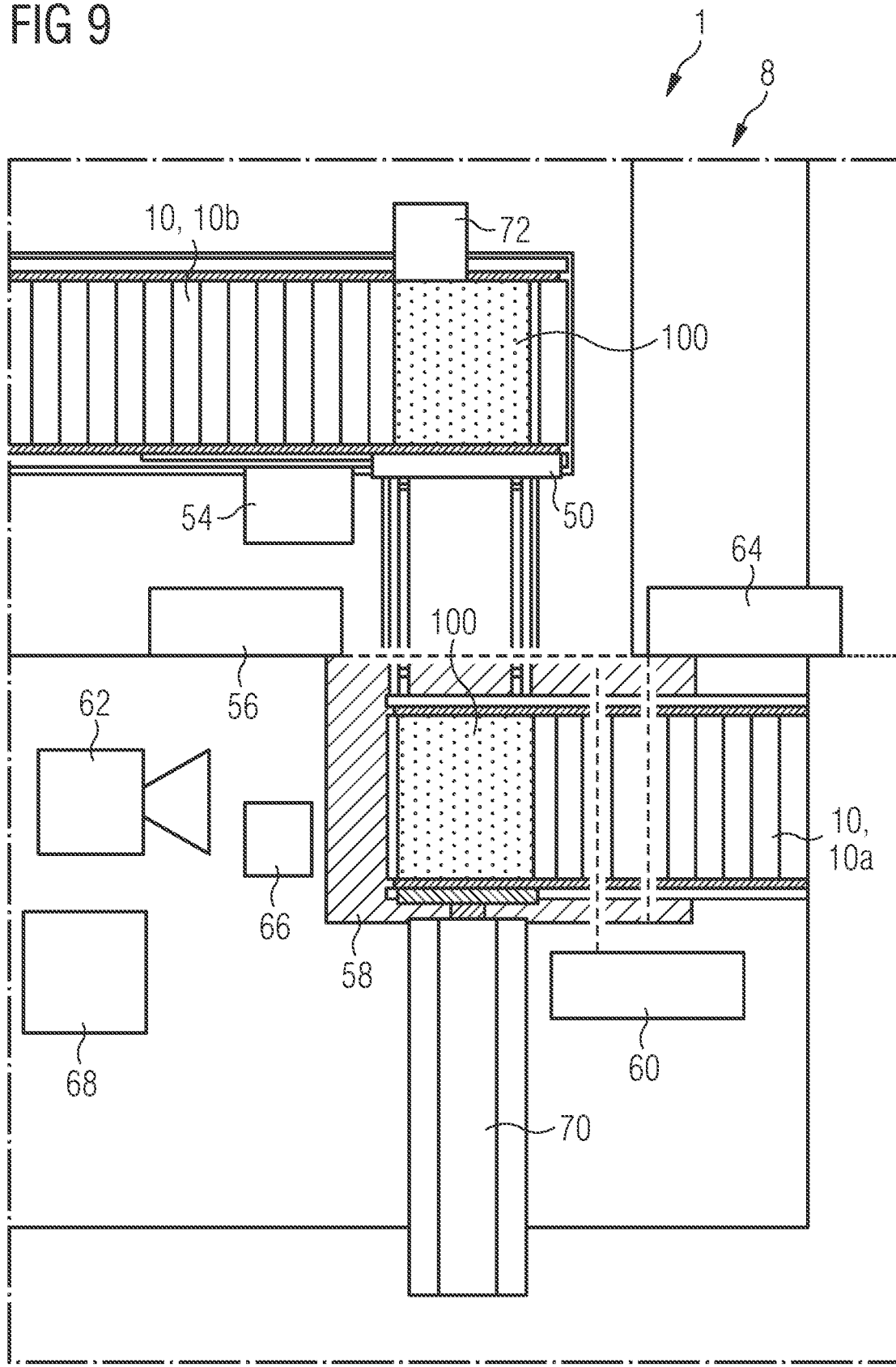
FIG. 9 shows a goods receiving area of the system for sterilizing sterilization units according to an embodiment in a schematic representation.
Figure 10:
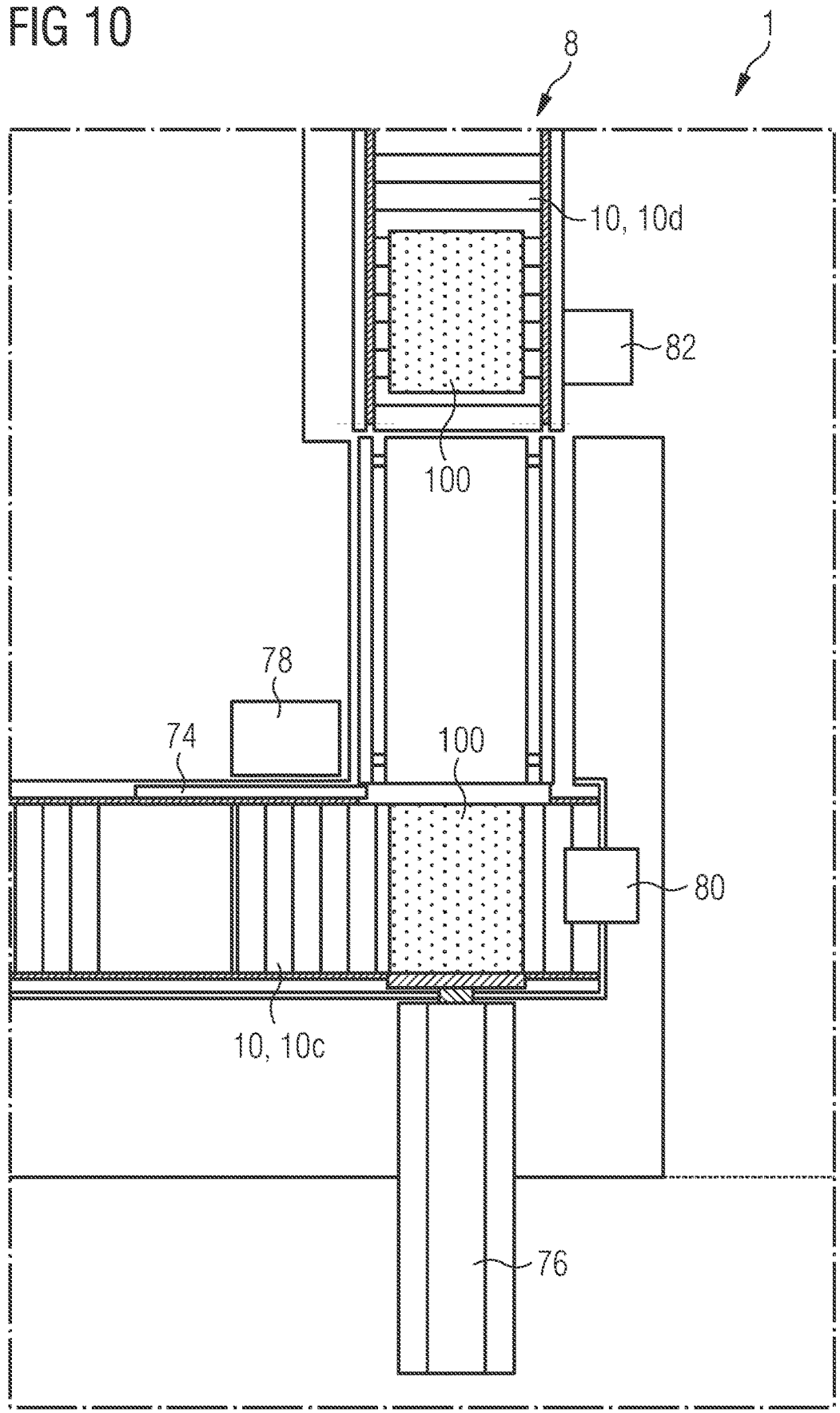
FIG. 10 shows a goods issuing area of the system for sterilizing sterilization units according to an embodiment in a schematic representation.

FIG. 9 illustrates the goods receiving area of the conveyance system 8 according to a possible design of the present disclosure.

The introduction of sterilization units 100 into the hot cell B1 via the goods receiving area is realized via a pneumatically driven bulkhead 50 with end-position sensors 54 and a pneumatic slide 70, which has a feed cylinder. The bulkhead 50 is typically opened only for introducing sterilization units 100 into the irradiation chamber or into the hot cell B1. A sensor 56 detects the entry region in front of the bulkhead 50, in order to detect whether the entry opening is free, and the bulkhead 50 can be closed.

The direct access for personnel via the goods receiving area is, as a rule, prevented by a housing 58 and the bulkhead 50. Furthermore, an optical sensor 60 and a registration device 62 is arranged on the entry side. The introduction of a sterilization unit 100 from the entry-side roller conveyor 10a into the housing 58 is detected by an optical sensor 60 and the registration device 62, which is designed to read out the coded information assigned to the individual sterilization units 100. The registration device 62 is, for example, designed as a barcode or QR code scanner. An additional optical sensor 64 is designed to detect the type of sterilization unit 100. For example, the optical sensor 64 detects the vertical extent of the sterilization unit 100 arriving at the entrance, in order to detect whether, for example, an individual standard carton or another type of irradiation container is present on the entry side. A further sensor 66 is designed to detect whether a sterilization unit 100 is located at the entry position within the housing 58 and is available for transport into the irradiation chamber or into the hot cell B1.

The registration device 62 at the entrance detects the barcodes and/or QR codes on the sterilization units 100 and determines therefrom the assigned irradiation container type. A control device 68 in an exemplary application case determines the specific type of sterilization unit 100 at the goods receiving area from the irradiation container type in conjunction with the height information detected by means of the optical sensor 64.

The introduction of the irradiation containers or sterilization units 100 into the irradiation chamber or into the hot cell B1 takes place by means of a pneumatic slide 70. The controlled coordination of the pneumatic slide 70 with the remaining components of the conveyance system 8 shown by way of example in FIG. 9 for re-conveying sterilization units 100 occurs preferably with the aid of potential-free contacts.

Reaching the transfer point to the irradiation chamber is detected by means of the sensor 66. If the transfer point is reached, then the following actions, in particular, in sequence, are carried out by the operational control system implemented in the control device 68:
- the bulkhead 50 for the irradiation chamber or for the hot cell B1 is opened, if sensor 72 reports that the position behind the bulkhead 50 is not occupied;
- when the bulkhead 50 is opened, the sterilization unit 100 is pushed by means of the pneumatic slide 70 through the bulkhead 50 by the outer roller conveyor 10a onto the inner roller conveyor 10b;
- sensor 72 registers whether a sterilization unit 100 is located in the region behind the bulkhead 50, whereupon the pneumatic slide 70 is retracted;
- the bulkhead 50 is closed;
- the end positions of the bulkhead 50 are monitored by sensor.

The housing 58 serves, in particular, to prevent the access for personnel to the irradiation chamber when the bulkhead 50 is opened. The entry to the housing 58 is monitored with the aid of the optical sensor 60 and the registration device 62. If the sensor 60 detects the presence of an object and the sensor 66 at the same time detects that the position within the housing 58 is free, then as a further precondition, the registration device 62 must read-in a valid barcode or QR code, so that the automatic conveyance process can be set into motion. The bulkhead 50 is only opened in the event of a valid QR code for the duration of the pushing through of a sterilization unit 100. The duration of the opening of the bulkhead 50 is monitored over time. The sensors 54, 56, 60, 64, 66 are part of an entry-side monitoring of the system 1. If a safety-related incident should be detected, then the output of a corresponding error message takes place, for example, via a user interface, in particular, a display device, a monitor, a computer or the like and/or an operational shut-down of the system 1 with the lowering of the radiation source 2 by means of automatic actuation of the lifting device 6. Preferably, the closed bulkhead 50 is automatically locked in the event that the sensor 72 detects no obstacle. In the event of a blocking, an automatic actuation of the pneumatic slide 70 and/or of the bulkhead 50, for example, can take place, in order, for example, to clear the entrance region.

At the exit of the conveying path from the irradiation chamber or from the hot cell B1 a further, pneumatically operated bulkhead 74, a further pneumatic slide 76 with feed cylinder and further sensors 78 designed for the detection of end positions is arranged. The bulkhead 74 is typically opened only for bringing sterilization units 100 out of the irradiation chamber. In the embodiment, in particular, a further registration device for reading out the information assigned to the sterilization units 100 is additionally arranged at the exit of the conveyance system 8.

Removing sterilization units 100 from the system 1 typically takes place as follows: The irradiated and sterilized sterilization units 100 are transported by roller conveyors 10, 10c in the lower plane H1 (see also FIG. 5) to the end of the conveying path of the hot cell B1 or of the irradiation region, at which a further sensor 80 is arranged. The sensor 80 is accordingly designed to detect the presence of objects in the end-side region of the roller conveyor 10c. If a sterilization unit 100 is detected there, then with the aid of the control implemented in the control device 68 the bulkhead 74 is automatically opened, provided that no object is located in the entry-side region of the outer roller conveyor 10d. This position is monitored by a further sensor 82. When the bulkhead 74 is opened, the pneumatic slide 76 is automatically activated and the sterilization unit 100 to be removed is conveyed onto the outer roller conveyor 10d. The sensor 82 registers this transport process. After the sensor 82 responds, the pneumatic slide 76 is automatically retracted. Subsequently, the bulkhead 74 is closed. In the event that an object should be located in the region of the sensor 82, the above described clock cycle of the system 1 cannot be carried out. It can be provided for this incident, to automatically stop the conveyance system 8 and to automatically lower the radiation source 2 with the aid of the lifting device 6 into the basin 4.

In order to prevent the access for personnel to the irradiation region when the bulkhead 74 is opened, the bulkhead 74, as a rule, is only opened for removing an individual sterilization unit 100. Subsequently, the bulkhead 74 is automatically closed again. The duration of the opening of the bulkhead 74 is monitored over time. The sensors 78, 60, 82 are, in particular, part of an automatic monitoring. If at least one component responds to this monitoring, then, for example, the output of a corresponding error message takes place via a user interface, in particular, a display device, a monitor, a computer or the like. Alternatively, or additionally, for example, an operational shut-down of the system 1 takes place with lowering the radiation source 2 into the basin 4 by means of automatic actuation of the lifting device 6.

The control device 68 indicated only schematically in FIG. 9 comprises in an embodiment several components, such as, for example, processors, controllers, computers, servers, clients and/or programmable logic controllers (PLC units). The control technology of the system 1 comprises, in particular, several PLC units for the operation and/or the safety-related control. In particular, in embodiments, at least one control is provided for monitoring the conveyance system 8, for lifting and lowering the radiation source 2 and/or for actuating auxiliary systems, such as, for example, a ventilation system.

A data server, for example, assumes the management of the parametrization data, records measurement data, documents the sterilization process and provides the data for the user, for example, with the aid of conventional computers, such as, for instance, PCs or laptops. The control device 68 can comprise, in particular, several computers interconnected in a wireless or wired manner with one another, in particular, computers, servers and/or clients.

The controls implemented in the control device 68 can, for example, serve different purposes, such as, for instance, for the control of the conveyance system 8 taking into account the predetermined clock cycle, the throughput time and the monitoring of the number of circulations, in order to ensure an as seamless a monitoring as possible of the irradiation. Another possible purpose can relate to the control of the lifting device 6 for the radiation source 2 or the actuation and monitoring of external components and auxiliary systems. In embodiments, the control also serves for the processing and documentation of the data from the conveyance system 8 or the measurement system. In embodiments, the control serves, in particular, for the processing and documentation of the sensor data detected by means of the sensors 56, 60, 64, 66, 72, 78, 80, 82. At least one control serves, in particular, for monitoring the seamless and proper transport preferably of all sterilization units 100. With the aid of a user interface, in embodiments, in particular, conveyances processes and the status of the system 1 can be displayed in an animated manner.

The products to be sterilized are typically provided in sterilization units 100, for example, in containers or standardized cardboard boxes, at the beginning of the conveyance system 8 on the roller conveyors 10 of the upper horizontal plane H1. The containers or cardboard boxes, from which the sterilization units 100 are formed, preferably have the same bottom surface, however, the individual sterilization units 100 can differ due to different cardboard box combinations in height. In order to realize as great a utilization of the system 1 as possible, it is advantageous to operate the conveyance system 8 in cyclical operation. A conveyance section F3, F4, F5, F6, F7, F8, F9, F10 realized, in particular, by a lifting beam conveyor 12 corresponds, for example, to the length of 6 to 9 standardized sterilization units 100. In particular, in each case a further sterilization unit 100 can be arranged on the roller conveyors 10 in the region of the transverse slide 14 and the lifts 16. Cyclical operation of the conveyance system 8 means here, in particular, that a sterilization unit 100 is moved forward in steps by in each case one position per clock cycle.

During the regular conveyance operation of the conveyance system 8 the sterilization units 100, as described already above, are transferred from the outer belt conveyor 10a to an inner conveyor system via a kind of lock. At the entrance of the irradiation chamber the QR code of the sterilization units 100, for example, is read in and thus the required dose rate, the irradiation prescription and the required number of circulations are passed on to the control of the control device 68. A control, which is designed, in particular, so as to be fail-safe, tests the transferred data and in embodiments monitors the clock cycle, the circulation time and the number of circulations of the individual sterilization units 100 within the hot cell B1 and preferably all other safety-related functions. Such functions relate, in particular, to the access to the irradiation chamber, for example, via the goods receiving area or the goods issuing area. An operational control assumes the control, preferably of all relevant operations, in particular, of those of the conveyance system 8, such as, for example, the control of the conveyance system 8 taking into consideration the active irradiation prescriptions, the predetermined clock cycle and the number of circulations. In embodiments, this includes the actuation of the frequency converters for the roller conveyors 10 and/or the actuation of the frequency converters for the lifts 16 and/or the actuation of valves for the pneumatic conveyance technology in the irradiation region, in particular, the lifting beam conveyor 12 and/or the transverse slide 14 and/or the calculation of the dwell time or of the clock cycle on the basis of the read-out coded information, in particular, of an irradiation prescription. Further relevant control processes relate, in particular, to the actuation of the lifting device 6 for the radiation source 2 and/or the actuation and monitoring of external components and auxiliary systems and/or the detection of the room temperature and/or the actuation of refrigeration machines, in particular, with switching over to a redundant refrigeration machine and/or the actuation of cooling water pumps with automatic switchover, and/or the actuation of a filling level supplement and/or a generation of error messages from external units and/or the actuation of a ventilation technology and/or the monitoring of the conductivity of the water in a cold water circuit and/or the monitoring of the radiation level in the cold water circuit.

LIST OF REFERENCE SIGNS 1 system
2 radiation source
4 basin
6 lifting device
8 conveyance system
10 roller conveyor
12 lifting beam conveyor
14 transverse slide
16 lift
18 rotary plate
20 rail
22 feed drive
24 stamp
28 guide
30 push cylinder
32 supporting beam
34 lifting beam
36 feed cylinder
38 lifting cylinder
40 support
42 tensile element
44 frame
46 fixed bearing
48 vertical strut
50 bulkhead
54 sensor
56 sensor
58 housing
60 sensor
58 housing
60 sensor
62 registration device
64 sensor
66 sensor
68 control device
70 slide
72 sensor
74 bulkhead
76 slide
78 sensor
80 sensor
82 sensor
100 sterilization unit H1 lower horizontal plane
H2 upper horizontal plane
B1 irradiation chamber (hot cell)
B2 irradiation chamber (area with lower local dose rate)
B3 control room
B4 machine room
F conveyance direction
F1 .... F12 conveyance section
P position
PP position

What is claimed is:

1. A system for sterilizing sterilization units by radiation exposure, comprising:
a radiation source;
a conveyance system configured for transporting sterilization units through a sterilizing environment along a conveying path, the sterilizing environment being exposed to radioactive radiation from the radiation source, at least one conveyance section of the conveying path extending along the periphery of the radiation source,
the radiation source configured for emitting gramma radiation,
the conveyance system comprising at least one lifting beam conveyor with at least one stationary supporting beam and at least one movable lifting beam, the at least one movable lifting beam being movable with respect to the at least one stationary supporting beam in a longitudinal direction and a vertical direction,
the at least one stationary supporting beam having a central region between two fixed bearings, the central region being supported via at least one tensile-loaded tensile element, the at least one tensile-loaded tensile element being fastened to the central region and to at least one vertical strut, the at least one vertical strut being arranged in a region of at least one of the fixed bearings, in such a manner that the tensile element extends in a direction diagonal to the longitudinal direction and the vertical direction.

2. The system according to claim 1, wherein the lifting beam conveyor is configured to be operated pneumatically.

3. The system according to claim 1, wherein the tensile element is configured as a steel cable.

4. The system according to claim 1, wherein the movable lifting beam and/or stationary supporting beam is designed as a T-beam.

5. The system according to claim 1, wherein the at least one tensile element is at least two tensile elements supporting the central region, the at least two tensile elements are fastened to opposite vertical struts, the opposite vertical struts being arranged respectively in the region of one of the fixed bearings.

6. The system according to claim 1, wherein the radiation source is stored in a basin filled with water when the system is inactive, the system further comprising a lifting device configured to lift the radiation source out of the basin filled with water and to lower the radiation source into the basin filled with water.

7. The system according to claim 1, wherein the at least one conveying section of the conveying path includes at least two conveyance sections running in horizontal planes spaced apart from one another in the vertical direction.

8. The system according to claim 1, wherein the at least one conveying section of the conveying path includes at least two conveyance sections arranged above one another in the vertical direction and aligned parallel to one another, wherein the conveyance sections arranged above one another extend along the periphery of the radiation source.

9. The system according to claim 8, wherein the at least two conveyance sections arranged above one another are connected via at least one lift, the at least one lift being configured to transport the sterilization units to be conveyed in the vertical direction.

10. The system according to claim 9, wherein the at least one lift is configured as a pneumatic lift.

11. The system according to claim 8, wherein the at least two conveyance sections arranged above one another in the vertical direction and aligned parallel to one another are configured as lifting beam conveyors within each case stationary supporting beams and movable lifting beams, wherein a lifting motion of the movable lifting beams arranged above one another is driven in the vertical direction by at least one common lifting cylinder.

12. The system according to claim 1, wherein the conveying path has at least two conveyance sections arranged in a horizontal plane and running parallel to one another.

13. The system according to claim 1, wherein the at least one conveying section of the conveying path includes at least one conveyance section comprising a roller conveyor.

14. The system according to claim 1, wherein the at least one conveying section of the conveying path includes at least one conveyance section comprising a rotary plate.

15. The system according to claim 14, the at least one conveying section of the conveying path includes at least two conveyance sections arranged above one another and connected via at least one lift, the at least one lift being configured to transport the sterilization units to be conveyed in the vertical direction, wherein the rotary plate is configured as the lift or is arranged on the lift.

16. The system according to claim 1, wherein a pneumatically driven transverse slide is configured to convey the sterilization units by translational movement over the at least one conveying section of the conveying path.

17. The system according to claim 1, further comprising at least one registration device arranged at the entrance of the conveying path, the at least one registration device being configured to read out coded information assigned to the sterilization units to be sterilized.

18. The system according to claim 17, wherein the at least one registration device is configured to optically read out coded information applied to the sterilization units.

19. The system according to claim 17, further comprising sensors arranged along the conveying path, the sensors being configured to detect data containing information about a progress of the transport of the respective sterilization unit.

20. The system according to claim 19, wherein the registration device and/or the sensors is or are connected to a control device, the control device being configured to adapt at least one process parameter depending on the read-out coded information and/or the data detected by sensor, depending on a dose energy to be applied.

21. A method for operating a system for sterilizing sterilization units by radiation exposure, the system comprising a conveyance system for transporting sterilization units through a sterilizing environment along a conveying path, the sterilizing environment being exposed to radioactive radiation from a radiation source, at least one conveyance section of the conveying path extending along a periphery of the radiation source, the sterilization of the sterilization units taking place by exposure to gamma radiation from the radiation source, the method comprising:
transporting the sterilization units at least in sections along the conveying path by at least one lifting beam conveyor, the at least one lifting beam conveyor comprising at least one stationary supporting beam and at least one movable lifting beam, the at least one movable lifting beam being movable with respect to the stationary supporting beam in a longitudinal direction and a vertical direction, the at least one stationary supporting beam having a central region between two fixed bearings, the central region being supported via at least one tensile-loaded tensile element, the at least one tensile-loaded tensile element being fastened to the central region and to at least one vertical strut, the at least one vertical strut being arranged in a region of at least one of the fixed bearings, in such a manner that the tensile element extends in a direction diagonal to the longitudinal direction and the vertical direction; and exposing the sterilization units individually to different dose energies in a continuous operation of the system in such a manner that an irradiation cycle is not thereby interrupted, wherein the at least one lifting beam conveyor is individually controlled with regard to its clock frequency and conveying speed in order to apply different target doses.

22. The method according to claim 21, wherein coded information is individually assigned to each of the sterilization units, which information is read out at least at the entrance of the conveyance system, wherein the coded information characterizes at least a dose energy to be applied.

23. The method according to claim 22, wherein a control unit determines a process parameter determined by the system depending on the read-out coded information.

24. The method according to claim 22, wherein the position of the sterilization units along the conveying path within the sterilizing environment is detected by a sensor.

* * * * *